US009353025B2

(12) United States Patent
Duff et al.

(10) Patent No.: US 9,353,025 B2
(45) Date of Patent: *May 31, 2016

(54) PROCESS FOR SELECTIVE REMOVAL OF ACETYLENES FROM GASEOUS STREAMS

(71) Applicant: TPC Group LLC, Houston, TX (US)

(72) Inventors: Joseph G. Duff, League City, TX (US); Cecil G. McFarland, League City, TX (US)

(73) Assignee: TPC GROUP LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/799,808

(22) Filed: Jul. 15, 2015

(65) Prior Publication Data

US 2015/0315107 A1    Nov. 5, 2015

Related U.S. Application Data

(63) Continuation of application No. 13/332,985, filed on Dec. 21, 2011, now Pat. No. 9,115,038.

(60) Provisional application No. 61/459,978, filed on Dec. 22, 2010.

(51) Int. Cl.
| *B01D 53/02* | (2006.01) |
| *C07C 7/148* | (2006.01) |
| *B01J 23/78* | (2006.01) |
| *B01J 23/94* | (2006.01) |
| *B01J 37/02* | (2006.01) |
| *B01J 37/18* | (2006.01) |

(52) U.S. Cl.
CPC ............... *C07C 7/1485* (2013.01); *B01J 23/78* (2013.01); *B01J 23/94* (2013.01); *B01J 37/0225* (2013.01); *B01J 37/18* (2013.01); *Y02P 20/584* (2015.11)

(58) Field of Classification Search
CPC ........... B01D 53/02; B01D 53/56; B01J 8/00; C07C 11/24
USPC ........................................................ 423/245.1
See application file for complete search history.

(56) References Cited

U.S. PATENT DOCUMENTS

| 2,379,670 | A | 7/1945 | Welling et al. |
| 3,476,824 | A | 11/1969 | Woskow |
| 3,728,412 | A | 4/1973 | Johnston et al. |
| 4,009,126 | A | 2/1977 | McFarland |
| 4,075,256 | A | 2/1978 | Foster et al. |
| 4,083,887 | A | 4/1978 | Foster et al. |
| 4,513,159 | A | 4/1985 | McFarland |
| 4,658,080 | A | 4/1987 | McFarland |
| 4,695,661 | A | 9/1987 | Homann et al. |
| 9,115,038 | B2 * | 8/2015 | Duff .................... B01J 23/78 |
| 2004/0012275 | A1 | 1/2004 | Thery et al. |

FOREIGN PATENT DOCUMENTS

CA        1034148 A1    7/1978

OTHER PUBLICATIONS

International Search Report of PCT/US2011/066434, dated Jul. 3, 2012.
Written Opinion of PCT/US2011/066434, dated Jul. 3, 2012.
International Preliminary Report on Patentability of PCT/US2011/066434, dated Apr. 8, 2013, together with Amendment and Response to Written Opinion of the International Preliminary Examining Authority Under PCT 66.3, dated Oct. 5, 2012 and Feb. 6, 2013.
Revised International Preliminary Report on Patentability in PCT/US2011/066434, dated Apr. 8, 2013.

* cited by examiner

*Primary Examiner* — Edward Johnson
(74) *Attorney, Agent, or Firm* — Michael W. Fenell

(57) ABSTRACT

The present discloses a process and catalyst therefor to selectively remove acetylenes from gaseous streams in the vapor phase. The process is particularly suitable for high yield recovery of olefinic hydrocarbons from gaseous streams in refinery processes.

15 Claims, 2 Drawing Sheets

PROCESS FOR SELECTIVE REMOVAL OF ACETYLENES FROM GASEOUS STREAMS

CLAIM FOR PRIORITY

This application is a continuation application based on U.S. patent application Ser. No. 13/332,985, of the same title filed Dec. 21, 2011. U.S. patent application Ser. No. 13/332,985 is based on U.S. Provisional Application No. 61/459,978 also of the same title filed Dec. 22, 2010. The priorities of U.S. patent application Ser. No. 13/332,985 and U.S. Provisional Application No. 61/459,978 are hereby claimed and their disclosures incorporated herein by reference.

TECHNICAL FIELD OF THE INVENTION

This invention relates, in part, to a process for the selective removal of acetylenic impurities and carbonyl impurities from gaseous hydrocarbon streams.

BACKGROUND OF THE INVENTION

The present invention relates to a process for the selective removal of acetylenic and carbonyl impurities, especially acetylenic impurities, from gaseous streams without significantly affecting the recovery of the desired hydrocarbons. The process of this invention is particularly useful for the removal of acetylenic impurities from gaseous streams of organic compounds.

The terms "acetylenes" or "acetylenic impurities" are used interchangeably herein to denote acetylene, vinyl acetylene, methyl acetylene, ethyl acetylene and the like. Such compounds are often found as impurities in various organic product streams. For example, the oxidative or non-oxidative dehydrogenation of C4-C8 hydrocarbons having at least one

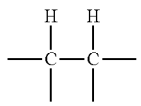

grouping to produce the corresponding ethylenically unsaturated hydrocarbons produces small amounts of acetylenes. Similarly, in the production of olefinic hydrocarbons by the cracking of hydrocarbon feed streams, certain quantities of acetylenes are produced. Some ethylene recovery processes, for example, the cuprous salt method, necessitate that the acetylenes be first removed, since acetylene reacts with the cuprous ions to form an explosive compound. Furthermore, ethylene utilized for the purpose of polymerization requires an almost total removal of acetylenes.

Thus, a great effort has been expended to develop methods for removing acetylenes from organic streams, particularly C2-C8 paraffinic and olefinic hydrocarbons. Two approaches have been employed (1) physical, involving distillations, extractions, extractive distillation and various combinations of physical processes and (2) catalytic. In the former process, if the concentration of acetylenic impurities is high, it may reach dangerous levels where detonation can occur. Thus, catalytic approaches have generally been preferred.

Some catalytic approaches in the art are described U.S. Pat. Nos. 3,476,824; 3,728,412; 4,009,126; 4,075,256; 4,083,887; 4,513,159; 4,658,080; and United States Patent Application Publication No. US 2004/0122275 which discloses are incorporated herein in their entirety. Some of the catalytic processes involve hydrogenating the acetylenic impurities back to alkenes and alkanes. However, this approach could result in some loss of the desired alkenes and alkadienes.

Thus, it would be preferable to find a process for selectively removing most of the acetylenic impurities (e.g., at least 80%, preferably at least 95%) from a gaseous stream without significantly affecting the recovery of the monoolefins and diolefins, particularly the desired diolefins. It would be preferable to recover at least 95% of the desired diolefins in the process.

SUMMARY OF THE INVENTION

The present invention is directed processes for selectively removing acetylenic impurities in a gaseous stream. The gaseous stream would contain other organic compounds, particularly C1 to C9 unsaturated hydrocarbon monoolefins and diolefins which would be the principal or desired products of the stream. Preferred hydrocarbon monoolefins and diolefins would have 2 to 8 carbon atoms and more preferably 4 to 6 or 8 carbon atoms. The instant process removes the acetylenic impurities to less than 10 ppm and still more preferably to less than 5 ppm. The process is especially suitable for removing the acetylenic impurities and recovering most of the diolefins. The inventive process is similarly effective for removing oxygenates such as aldehydes which may be present.

Briefly, the process comprises contacting an input stream of organic compounds containing acetylenic impurities in the vapor phase, along with steam, and in some embodiments in the substantial absence of added oxygen and hydrogen in the input stream, with a catalyst for removing most of said acetylenic impurities from said input stream, said catalyst most preferably comprising as the major cation elements by weight Ba, Ni, Na and Fe. Zinc catalyst components tend to be expensive and/or difficult to process and their absence is accordingly highly desirable.

In one embodiment of the invention, a zinc-free catalyst is used to remove impurities from an input stream having one or more hydrocarbons, acetylenic impurities and steam selected from streams (a), (b), (c), (d), or (e), wherein stream (a) comprises ethylene in at least 75 mol % based on the hydrocarbon, acetylenic impurities and steam content of the stream; stream (b) comprises propylene in at least 75 mol % based on the hydrocarbon, acetylenic impurities and steam content of the stream; input stream (c) comprises styrene in at least 75 mol % based on the hydrocarbon, acetylenic impurities and steam content of the stream; input stream (d) comprises isoprene in at least 75 mol % based on the hydrocarbon, acetylenic impurities and steam content of the stream; and stream (e) comprises less than 50 mol % C4 hydrocarbons based on the hydrocarbon content of the input stream.

In another embodiment, the present invention is directed to a vapor phase process for the selective removal of at least 95 mole % of acetylenic impurities from an input gaseous stream wherein said input stream comprises C1 to C9 unsaturated hydrocarbon monoolefins and diolefins, acetylenic impurities and steam, with no added hydrogen or oxygen, wherein the process comprises contacting said input stream in the vapor phase at a temperature in the range of about 480° F. to about 1650° F. with a solid zinc-free catalyst, said catalyst being preferably derived from oxides, carbonates and/or hydroxides of Ba, Ni, Na and Fe, wherein said Ba is present in about 0.25-40 wt % on dry basis of said catalyst, Ni is present in about 0.25-20 wt % on dry basis of said catalyst, Na is present in about 0.25-40 wt % on dry basis of said catalyst, with the remainder being Fe, and recovering an output stream wherein said output stream retains at least 95 mole % of said C1 to C9 unsaturated hydrocarbon diolefins but lacks at least 80 mole % of said acetylenic impurities.

BRIEF DESCRIPTION OF THE DRAWINGS

The present invention is described in connection with by the attached Figures, wherein.

DETAILED DESCRIPTION OF THE INVENTION

Figure 1:
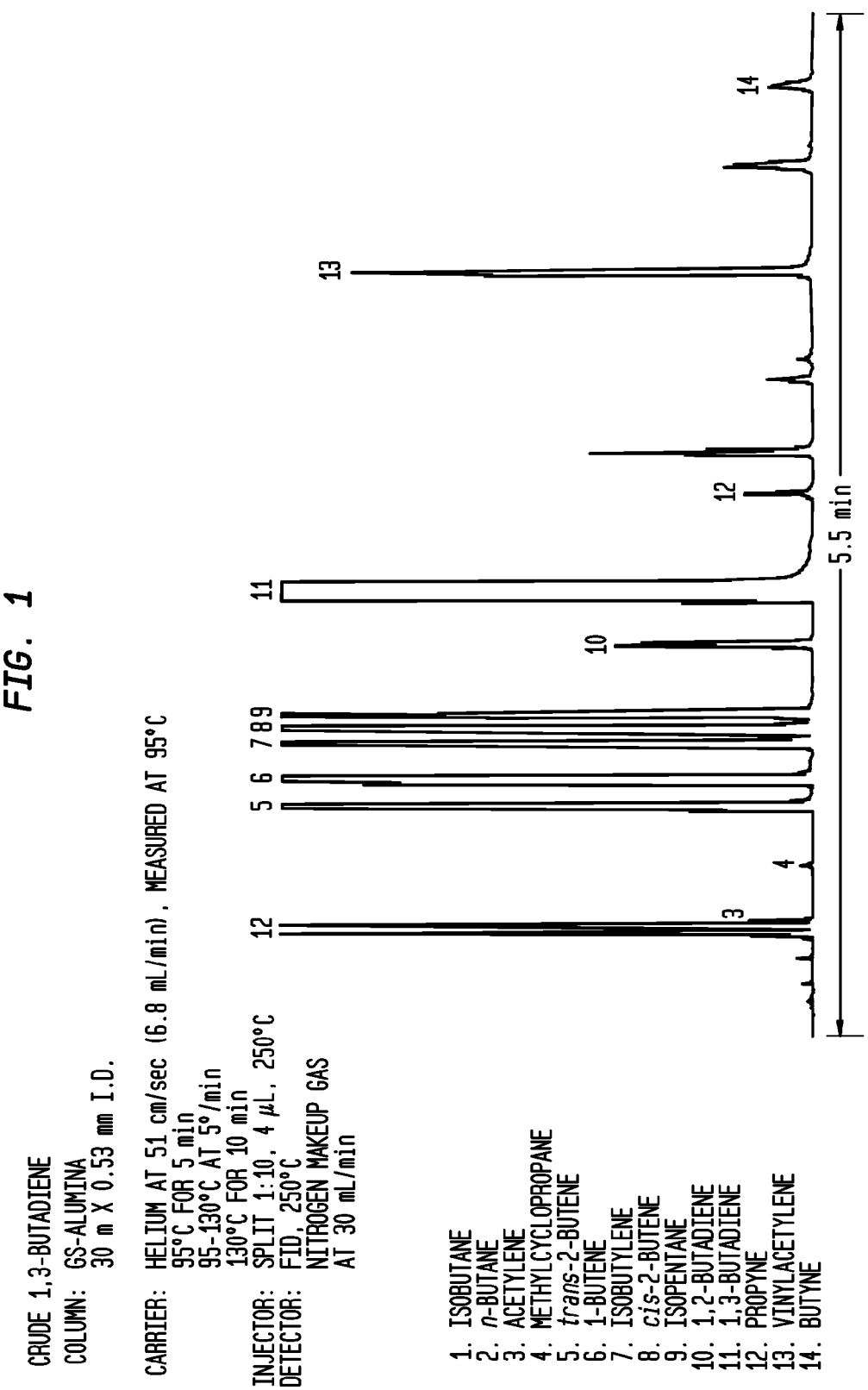
FIG. 1 is a gas chromatograph of crude 1,3-butadiene hydrocarbon stream containing acetylenic impurities (peaks 12, 13 and 14) to be purified.

The invention is described in detail below with reference to the drawings and examples. Such discussion is for purposes of illustration only. Modifications within the spirit and scope of the present invention, set forth in the appended claims, will be readily apparent to one of skill in the art. Terminology used throughout the specification and claims herein is given its ordinary meaning except as more specifically defined; for example, acetylene removal is calculated as the difference between the acetylene content of the input stream minus the acetylene content of the output stream.

Ba, Ni, Na and Fe content of the catalyst is based on the relative metal oxide content of catalytic metal oxides in the catalyst for convenience as is commonly done in the art. See U.S. Pat. No. 4,695,661, the disclosure of which is incorporated herein by reference. In order to determine content of these metals, the catalyst is placed in an oven overnight at 480° C. in air and the catalytic metal oxide content is thereafter measured by x-ray diffraction and infra red spectroscopy or other suitable technique(s). A catalyst analyzed with 10% barium oxide based on the catalytic metal oxide content (i.e oxides of Ba, Na, Ni and Fe in the examples) is referred to as a catalyst containing 10% barium on a dry basis of said catalyst herein.

The acetylenic impurities are a serious contaminant in the unsaturated hydrocarbon product stream and must be essentially substantially completely removed in order to have a product of suitable purity, i.e., a product having on the order of not more than a few parts per million acetylenic impurities. The essentially substantially complete removal of the acetylenic compounds is quite difficult for several reasons. Principally, the acetylenic compounds constitute only a very minor percentage of the gaseous stream to be purified. Normally, acetylenic impurities will constitute less than 5.0 mol percent of the gaseous stream. Generally the gaseous stream will contain at least about 0.5-2.0 mol percent acetylenic impurities based on the other organic compounds present such as the ethylenically unsaturated hydrocarbons. Their low concentration in the stream makes acetylenes quite difficult to remove. Moreover, azeotropes may form between the acetylenic impurities and the various other hydrocarbons present.

The organic compounds which can be treated according to the present process generally have 1 to 9 carbon atoms. The major portion of the stream can be saturated and/or unsaturated (excluding acetylenic unsaturates) compounds and may comprise straight chain and/or branched compounds, similarly the desired compounds may be cyclic, acyclic or aromatic or mixtures of the foregoing. An illustrative, typical hydrocarbon feed in the input stream may contain, for example, mixed butenes (isobutene, 1-butene, cis-2-butene, trans-2-butene, 1,3-butadiene etc.) with acetylenes (such as, for example, methyl acetylene, ethyl acetylene, vinyl acetylene and the like), any butanes, mixed C5 hydrocarbons or other hydrocarbons. An example hydrocarbon stream would be the crude mixed butane/butadiene stream from ethylene cracker or the mid-process stream in butane/butadiene purification.

A preferred group of compounds are hydrocarbons having 1 to 9 carbon atoms, typically monoolefins and diolefins. A more preferred group of compounds are hydrocarbons having 2 to 8 carbon atoms, typically monoolefins and diolefins. A still more preferred group of compounds are hydrocarbons having 4 to 8 carbon atoms, typically monoolefins and diolefins. The process is a purification and hence the acetylenic impurities are present in only minor amounts in comparison to the other organic compounds in the stream.

The preferred catalyst used in the inventive process typically contains the atoms of Ba, Ni, Na and Fe. However, no zinc or zinc compounds are present. The Ba, Ni, Na and Fe atoms may be present in the form of the metal compounds such as oxides, salts or hydroxides. Many of these metals, oxides, salts and hydroxides may change during the preparation of the catalyst, during heating in a reactor prior to use in the process of this invention, or are converted to another form under the described reaction conditions, but such materials still function as an effective catalyst in the defined process to impart the removal or destruction of acetylenic impurities. However, some metal compounds are more effective than other compounds of the same metal and, therefore, the compound giving the most effective results can be chosen. Preferably, catalysts, which are solid under the conditions of acetylene removal, will be used. Preferably, the compound will exhibit some basicity, e.g., as in the case of oxides, carbonates, or hydroxides.

The amount of barium or other alkaline earth element employed is about 0.25-40 wt % on dry basis based on total catalytic metal oxide weight (excluding any support or diluents), preferably about 1-20 wt % on dry basis of said catalyst, and more preferably about 5 to 15 or 5 to 10 weight percent. The amount of nickel employed is about 0.25-20 wt % on dry basis based on total catalytic metal oxide weight (excluding any support), preferably about 1-15 or 1-10 wt % on dry basis of said catalyst, and more preferably about 7 to 15 weight percent. The amount of sodium or other alkali metal employed is about 0.25-40 wt % on dry basis based on total catalytic metal oxide catalyst weight (excluding any support), preferably about 0.5-30 wt % on dry basis of said catalyst, and more preferably 10 to 25 or 10 to 15 weight percent. The remaining amount of catalytic metal oxide in the catalyst is typically iron. In a typical experiment, the amount of iron is in the range of about 30-75 or 30-55 weight %, preferably 30-65 or 30-50 weight %, and more preferably about 35-45 weight %.

In an illustrative preparation of the catalyst, yellow iron oxide ($Fe_2O_3 \cdot H_2O$, dry powder), barium carbonate ($BaCO_3$, dry powder), basic nickel carbonate (also known as Nickel(II) carbonate hydroxide hydrate, dry powder), sodium hydroxide (NaOH, as aqueous solution) are used. The dry ingredients are blended to give a uniform powder. Water is added and mixed well. The mix is dried to remove the water. Exposure to air is avoided after drying. The catalyst is reduced in the reactor before interacting with the incoming stream. Some suitable reduction methods are reduction at high temperature with hydrogen, or natural gas or other suitable reducing agents. Such suitable methods are described, for example, in the afore-mentioned U.S. Pat. No. 4,513,159.

The catalyst is preferably in solid form. If desired, it can be extruded and dried into a desired shape. The catalyst may be used as such or may be coated or otherwise supported on non-reactive, inert catalyst carriers ("supports"). Catalyst carriers are known in the art and include such compounds as alumina, silica, silicon carbide, pumice, glass and so forth. Diluents may also be incorporated into the catalyst so long as the diluent does not prevent the catalyst from functioning. Preferably the carrier should be low surface and low acidity. When carriers are used, the amount of catalyst on the carrier will generally be between about 5 and 75 weight percent of the total weight of the active catalytic material plus carrier. The present process is not an oxidative dehydrogenation since the input stream does not contain substantial amounts of oxygen. The input additionally lacks substantial amounts of added hydrogen. The molar ratio of oxygen content to hydrocarbon content in the input stream is generally less than 0.01, preferably less than 0.005 and more preferably less than 0.0025. While not intending to be limited to any mechanism, it is believed that the present process is a carbonization of the acetylenes. The output stream contains hydrogen presumably the hydrogen removed from the acetylenes which then become carbonized, as well as that produced by water gas shift between steam and said carbonized product:

(e.g. H2O+C→H2+CO(ΔH=+131 kJ/mol)

CO(g)+H2O(v)→CO2(g)+H2(g)(ΔH=−41.1 kJ/mol).

In an illustrative description of the present process, the input hydrocarbon mix containing the acetylenic impurities is vaporized and mixed with steam at a desired steam/hydrocarbon ratio. The steam/hydrocarbon ratios mol/mol are generally about 1-25 respectively, preferably being about 2 to 15 steam/HC, more preferably being about 3 to 8, and still more preferably about 3-5 steam/HC. The mix of hydrocarbon and steam ("the input stream") is run over a bed of the catalyst as described above at a targeted liquid hourly space velocity ("LHSV") based solely on the hydrocarbon feed. The targeted LHSV may generally be in the range of 1-8, preferably 2-6 and more preferably 3-5. The temperature of the bed is controlled to be in the range about 480-1650° F. generally, about 600-1,400° F. preferably, about 900-1200° F. more preferably and about 900-1000° F. typically, by adjusting the steam temperature and/or providing external heat to the system. The pressure of the bed is controlled to be about 0-300 psia generally, about 2-200 psia preferably, about 10-50 psia more preferably and about 14-16 psia typically, by controlling off-gas pressure. The exit or effluent gas is cooled to condense water away from the hydrocarbons. The recovered hydrocarbon mix is sent for further purification to separate the hydrocarbons from the CO, CO₂ and hydrogen as needed.

After the catalyst has been used for a period of time it may be regenerated such as by controlled oxidation with air and/or with steam in the absence of hydrocarbon.

The following examples are only illustrative and are not intended to limit the invention. All percentages are by weight unless expressed otherwise.

Example 1

Preparation of Catalyst on Support

An acetylene removal catalyst was prepared as follows: 26.81 grams of Fe₂O₃.H₂O, 3.82 grams of BaCO₃, 7.27 gms of basic NiCO₃ were placed in a blender and dry mixed together to form a uniform powder. 8.38 grams of NaOH in 320 grams of water was added and the mix was made into a very thin yellow liquid. The liquid was poured into a 2 liter round bottomed glass flask containing 0.24 inch of 316 stainless steel packing. About 30 ml of additional was used to rinse the blender and lid into the round bottomed flask. The flask was placed on a rotovap and water was removed in vacuo at about 50-80° C. for about 0.5-2 hours or until the support appeared well coated and dry. The flask was removed from the rotovap and placed in an oven at about 110° C. overnight to dry. The coated support looked yellow to yellowish brown in color and it was kept away from air until use.

Prior to use for acetylene removal from the input stream of hydrocarbons, the catalyst is preferably reduced. The reduction could be carried out in a number of methods. For example, a flow of hydrogen through the catalyst for from 5 minutes to several hours, e.g., 5 hours at temperatures of about 500° F. to about 1600° F. was found suitable. Generally, the temperature of about 900-1100° F. was found adequate. Other reducing compounds such as n-butane could also be used to reduce the catalyst. The reduction seemed beneficial to the acetylenes removal.

Example 2

Acetylene Removal from a Hydrocarbon Mix

The equipment used was similar to the one described for acetylene removal in the afore-mentioned U.S. Pat. No. 4,513,159. The reactor was a 24 inch long, 1 inch I.D. stainless steel tube inserted in a 3100 watt furnace having three separate temperature control elements. The upper 8 inches serve as a steam super heater. The hydrocarbon feed was injected into the super heated steam prior to the steam entering a catalyst bed of about 10 inches length with inert support on top and bottom of the bed to fill the reactor. The effluent was sampled after cooling the outlet stream and condensing the water. Analyses were by gas chromatographic methods.

In typical runs, the hydrocarbon mix was vaporized and mixed with steam at a desired steam/hydrocarbon ratio. This input stream was run over the catalyst bed at a targeted LHSV based solely on the hydrocarbon feed composition. Temperature of the bed was controlled by adjusting the steam temperature and/or providing external heat to the system. The exit gas was cooled to condense water away from the hydrocarbons and analyzed. A typical run that was carried out on an input hydrocarbon stream containing butadienes to selectively remove the acetylenes and recover most of the butadienes is shown in Table 1:

TABLE 1

|  | In | Out | Remarks |
|---|---|---|---|
| Temp. |  |  | 1030° F. |
| LHSV (L/L/hr) |  |  | 2 |
| Steam/hydrocarbon ratio (mol/mol) |  |  | 4:1 |
| Butadiene content, mole %** | 52.7 | 52.4 | Recovery 99.4% |
| Acetylene content* mole %** | 1.40 | 0.01 | Acetylene removal: 99.6% |
| Carbon oxides (mol %)*** | 0.00 | 7.02 |  |
| Hydrogen (mol %)*** | 0.00 | 16.15 |  |

*Sum of methyl acetylene, ethyl acetylene and vinyl acetylene
**Butadiene content and acetylene content are based on hydrocarbon content only.
***Carbon oxides content and hydrogen content are given as percentage in the outlet sample.

Figure 2:
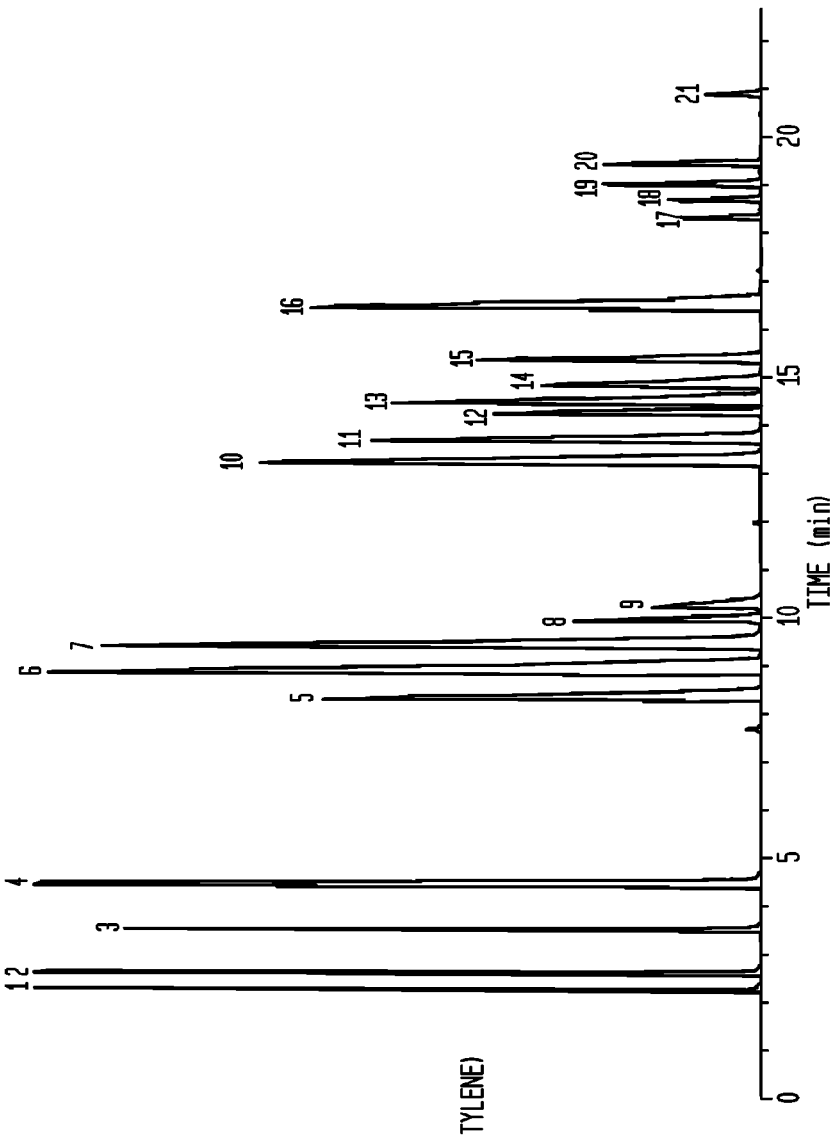
FIG. 2 is a gas chromatograph of a refinery gas stream containing mixtures of various C2-C6 hydrocarbons and acetylenic impurities (peak 9) to be purified.

Even though the foregoing Example illustrates the removal of acetylenes from a 1,3-butadiene input stream, the present invention is suitable for removal of acetylenic impurities from various other hydrocarbon streams too such as, for example, C2 gas streams (ethylene), C3 gas streams (propylene), C5 gas streams (isoprene), C6 gas streams (styrene) and the like. For example, gas streams containing at least 75 mol % C2 hydrocarbons, or at least 75 mol % C3 hydrocarbons, or at least 75 mol % C5 hydrocarbons or at least 75 mole % C6 hydrocarbons can be purified of acetylenes by methods similar to that as described above. It is further contemplated that the removal of acetylenes from such C2, C3, C5 or C6 hydrocarbon streams can be carried out with or without having a substantial absence of added oxygen and substantial absence of added hydrogen in the input stream. For example, an input stream containing a C2 (or C3 or C5 or C6) hydrocarbon mix and steam can be passed over a catalyst bed as described in the present invention under the inventive conditions and freed of at least 80 mol % of acetylenic impurities, irrespective of whether there is added oxygen or not, or added hydrogen or not, in the input stream. Generally, such embodiments also include cases where the gas is other than a stream consisting primarily of C4 hydrocarbons as shown in FIG. 1. For example, the invention may be used to purify a refining gas stream having the composition shown in FIG. 2 with or without added oxygen or hydrogen. Typically, the invention is used to purify hydrocarbon streams being less than 50 mol % C4 hydrocarbons with or without added oxygen and such streams may have less than 20 mol % or less than 10 mol % C4 hydrocarbons based on the hydrocarbon content. Such modifications are also to be considered as part of the present invention.

As can be seen clearly, the instant invention affords a novel process to selectively remove acetylenic impurities from a hydrocarbon mix without detrimentally affecting the desired diolefins.

There is provided in one aspect of the invention a vapor phase process for selective removal of at least 80 mole % of acetylenic impurities from an input gaseous stream wherein said input stream comprises C1 to C9 unsaturated hydrocarbon monoolefins and diolefins, acetylenic impurities and steam with or without substantial amounts of added hydrogen or oxygen, wherein said process comprises contacting said input stream in the vapor phase at a temperature in the range of about 250° C. (480° F.) to about 900° C. (1650° F.) with a solid zinc-free catalyst, said catalyst derived from and preferably including oxides, carbonates and/or hydroxides of Ba, Ni, Na and Fe, wherein said Ba is present in about 0.25-40 wt % on dry basis of said catalyst, Ni is present in about 0.25-20 wt % on dry basis of said catalyst, Na is present in about 0.25-40 wt % on dry basis of said catalyst, with the remainder being Fe, and recovering an output stream. The output stream retains at least 95 mole % of said C1 to C9 unsaturated hydrocarbon monoolefins and diolefins but lacks at least 80 mole % of said acetylenic impurities. Preferably, the process selectively removes at least 95 mol % of said acetylenic impurities. The selectively removed acetylenic impurities may include vinyl acetylene And the input stream optionally comprises C2 to C8 hydrocarbon compounds, acetylenic impurities and steam with no added hydrogen or oxygen. In some cases, the input stream contains less than 50% C4 hydrocarbons and in others, the input stream contains less than 25% C4 hydrocarbons, such as less than 20% C4 hydrocarbons. The process may be operated at temperature ranges from about 315° C. (600° F.) to about 760° C. (1400° F.) such as at temperature ranges from about 480° C. (900° F.) to about 650° C. (1200° F.) and at pressures of about 0-2.1 MPa (0-300 psia).

Ba may be present in about 1-20 wt % on dry basis of said catalyst, Ni may be present in about 1-10 wt % on dry basis of said catalyst, Na may be present in about 0.5-30 wt % on dry basis of said catalyst, with the remainder being Fe. A preferred process is where Ba is present in about 5-8 wt % on dry basis of said catalyst, Ni is present in about 7-9 wt % on dry basis of said catalyst, Na is present in about 10-14 wt % on dry basis of said catalyst, with the remainder being Fe. The catalyst may be prepared from barium carbonate, nickel carbonate, sodium hydroxide and iron oxide.

In some cases, the input stream contains about 1-2 mole % acetylenic impurities and said output stream contains less than 0.02 mole % acetylenic impurities and the output stream retains more than about 98 mole % of said C1 to C9 unsaturated hydrocarbon monoolefins and diolefins. Optionally, the output stream is cooled to remove water and additionally the process includes the step of regenerating the catalyst after use. Typically, said regeneration comprises controlled oxidation with air or steam in the absence of hydrocarbon.

In some embodiments, the molar ratio of oxygen content to hydrocarbon content in the input stream is less than 0.01.

In another aspect of the invention, there is provided a vapor phase process for selective removal of at least 80 mole % of acetylenic impurities from an input gaseous stream wherein said input stream comprises ethylene in at least 75 mol % based on the hydrocarbon content of the stream, acetylenic impurities and steam, further wherein said process comprises contacting said input stream in the vapor phase at a temperature in the range of about 250° C. (480° F.) to about 900° C. (1650° F.) with a solid zinc-free catalyst, said catalyst derived from and preferably including oxides, carbonates and/or hydroxides of Ba, Ni, Na and Fe, wherein said Ba is present in about 0.25-40 wt % on dry basis of said catalyst, Ni is present in about 0.25-20 wt % on dry basis of said catalyst, Na is present in about 0.25-40 wt % on dry basis of said catalyst, with the remainder being Fe, and recovering an output stream wherein said output stream retains at least 95 mole % of said ethylene but lacks at least 80 mole % of said acetylenic impurities.

In still another aspect of the invention, there is provided a vapor phase process for selective removal of at least 80 mole % of acetylenic impurities from an input gaseous stream wherein said input stream comprises propylene in at least 75 mol % based on the hydrocarbon content of the stream, acetylenic impurities and steam, further wherein said process comprises contacting said input stream in the vapor phase at a temperature in the range of about 250° C. (480° F.) to about 900° C. (1650° F.) with a solid zinc-free catalyst, said catalyst derived from and preferably including oxides, carbonates and/or hydroxides of Ba, Ni, Na and Fe, wherein said Ba is present in about 0.25-40 wt % on dry basis of said catalyst, Ni is present in about 0.25-20 wt % on dry basis of said catalyst, Na is present in about 0.25-40 wt % on dry basis of said catalyst, with the remainder being Fe, and recovering an output stream wherein said output stream retains at least 95 mole % of said propylene but lacks at least 80 mole % of said acetylenic impurities.

Yet another aspect of the invention provides a vapor phase process for selective removal of at least 80 mole % of acetylenic impurities from an input gaseous stream wherein said input stream comprises isoprene in at least 75 mol % based on the hydrocarbon content of the stream, acetylenic impurities and steam, further wherein said process comprises contacting said input stream in the vapor phase at a temperature in the range of about 250° C. (480° F.) to about 900° C. (1650° F.) with a solid zinc-free catalyst, said catalyst derived from and preferably including oxides, carbonates and/or hydroxides of Ba, Ni, Na and Fe, wherein said Ba is present in about 0.25-40 wt % on dry basis of said catalyst, Ni is present in about 0.25-20 wt % on dry basis of said catalyst, Na is present in about 0.25-40 wt % on dry basis of said catalyst, with the remainder being Fe, and recovering an output stream wherein said output stream retains at least 95 mole % of said isoprene but lacks at least 80 mole % of said acetylenic impurities.

Still yet another aspect of the invention provides a vapor phase process for selective removal of at least 80 mole % of acetylenic impurities from an input gaseous stream wherein said input stream comprises styrene in at least 75 mol % based on the hydrocarbon content of the stream, acetylenic impurities and steam, further wherein said process comprises contacting said input stream in the vapor phase at a temperature in the range of about 250° C. (480° F.) to about 900° C. (1650° F.) with a solid zinc-free catalyst, said catalyst derived from and preferably including oxides, carbonates and/or hydroxides of Ba, Ni, Na and Fe, wherein said Ba is present in about 0.25-40 wt % on dry basis of said catalyst, Ni is present in about 0.25-20 wt % on dry basis of said catalyst, Na is present in about 0.25-40 wt % on dry basis of said catalyst, with the remainder being Fe, and recovering an output stream wherein said output stream retains at least 95 mole % of said styrene but lacks at least 80 mole % of said acetylenic impurities.

There is also provided in another aspect of the invention, a vapor phase process for selective removal of acetylenic impurities from an input gaseous stream wherein said input stream comprises acetylenic impurities, steam, and hydrocarbons, with the proviso that the stream comprises less than 50 mol % C4 hydrocarbons based on the hydrocarbon content of the stream, further wherein said process comprises contacting said input stream in the vapor phase at a temperature in the range of about 250° C. (480° F.) to about 900° C. (1650° F.) with a solid zinc-free catalyst, said catalyst derived from and preferably including oxides, carbonates and/or hydroxides of Ba, Ni, Na and Fe, wherein said Ba is present in about 0.25-40 wt % on dry basis of said catalyst, Ni is present in about 0.25-20 wt % on dry basis of said catalyst, Na is present in about 0.25-40 wt % on dry basis of said catalyst, with the remainder being Fe, and recovering an output stream wherein said output stream retains at least 95 mole % of said ethylene but lacks at least 80 mole % of said acetylenic impurities.

The processes of the invention may be carried out wherein the process selectively removes at least 95 mol % of said acetylenic impurities and the selectively removed acetylenic impurities are vinyl acetylenes; optionally wherein said input stream contains less than 25% C4 hydrocarbons, such as wherein said input stream contains less than 20% C4 hydrocarbons.

In the various embodiments of the invention, one preferred catalyst is a catalyst comprising Ni, Fe, an alkali metal such as sodium and optionally an alkaline earth element such as Ba wherein Ni is present in an amount of 0.25-20 wt % on a dry basis of said catalyst and Fe is present in an amount of 30-75% on a dry basis of said catalyst. Such a catalyst may be made with or without zinc.

In the various embodiments of the invention, another preferred catalyst is a solid zinc-free catalyst, said catalyst comprising Ba, Ni, Na and Fe, wherein said Ba is present in an amount of 0.25-40 wt % on a dry basis of said catalyst, Ni present in an amount of 0.25-20 wt % on a dry basis of said catalyst, Na present in an amount of 0.25-40 wt % on a dry basis of said catalyst, and Fe is present in an amount of 30-75% on a dry basis of said catalyst.

While the invention has been described in detail, modifications within the spirit and scope of the invention will be readily apparent to those of skill in the art. In view of the foregoing discussion, relevant knowledge in the art and references discussed above in connection with the Background of the Invention, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A vapor phase process for selective removal of at least 80 mole % of acetylenic impurities from an input gaseous stream wherein said input stream comprises C1 to C9 unsaturated hydrocarbon monoolefins, diolefins and acetylenic impurities wherein said process comprises contacting said input stream in the vapor phase at a temperature in the range of 250° C. (480° F.) to 900° C. (1650° F.) with a solid zinc-free catalyst, said catalyst having the following metals only: Ni, Fe, alkali metal, and optionally alkaline earth element(s) wherein said Ni is present in an amount of 0.25-20 wt % on a dry basis of said catalyst and Fe is present in an amount of 30-75 wt % on a dry basis of said catalyst; and thereafter recovering an output stream wherein said output stream retains at least 95 mole % of said C1 to C9 unsaturated hydrocarbon monoolefins and diolefins but lacks at least 80 mole % of said acetylenic impurities.

2. The process of claim 1, wherein said process selectively removes at least 95 mol % of said acetylenic impurities.

3. The process of claim 1, wherein said selectively removed acetylenic impurities are vinyl acetylene.

4. The process of claim 1, wherein said temperature ranges from 480° C. (900° F.) to 650° C. (1200° F.).

5. The process of claim 1, wherein said catalyst is in a reaction zone at a pressure of from 0.014 to 2.1 MPa (2-300 psia).

6. The process of claim 1, wherein Ba is present in about 1-20 wt % on dry basis of said catalyst, Ni is present in about 1-15 wt % on dry basis of said catalyst, Na is present in about 0.5-30 wt % on dry basis of said catalyst, with the remainder of catalytic metal being Fe.

7. The process of claim 1, wherein said Ba is present in about 5-8 wt % on dry basis of said catalyst, Ni is present in about 7-9 wt % on dry basis of said catalyst, Na is present in about 10-14 wt % on dry basis of said catalyst, with the remainder being Fe.

8. The process of claim 1, wherein said catalyst is prepared from barium carbonate, nickel carbonate, sodium hydroxide and iron oxide.

9. The process of claim 1, wherein said input stream contains about 1-2 mole % acetylenic impurities and said output stream contains less than 0.02 mole % acetylenic impurities.

10. The process of claim 1, wherein said output stream retains more than about 98 mole % of said C1 to C9 unsaturated hydrocarbon monoolefins and diolefins.

11. The process of claim 1, additionally comprising the step of regenerating the catalyst after use.

12. The process of claim 11, wherein said regeneration comprises controlled oxidation with air or steam in the absence of hydrocarbon.

13. A zinc-free catalyst for selective removal of acetylenic impurities from a hydrocarbon stream, said catalyst having the following metals, only: Ni, Fe, alkali metal, and optionally alkaline earth element(s) wherein said Ni is present in an amount of 0.25-20 wt % on a dry basis of said catalyst, Fe is present in an amount of 30-75 wt % on a dry basis of said catalyst.

14. The zinc-free catalyst of claim 13, wherein Ba is present in 1-20 wt % on dry basis of said catalyst, Ni is present in 1-10 wt % on dry basis of said catalyst, Na is present in 0.5-30 wt % on dry basis of said catalyst, with the remainder of catalytic metal being Fe.

15. The zinc-free catalyst of claim 13, wherein Ba is present in 5-8 wt % on dry basis of said catalyst, Ni is present in 7-9 wt % on dry basis of said catalyst, Na is present in 10-14 wt % on dry basis of said catalyst, with the remainder of catalytic metal being Fe.

* * * * *